United States Patent [19]  
Richards et al.

[11] 4,014,049  
[45] Mar. 29, 1977

[54] ARTIFICIAL INTRAOCULAR LENS AND SUPPORTING SYSTEM THEREFOR

[75] Inventors: William Richards, Medway; Bernard Grolman, Worcester, both of Mass.

[73] Assignee: American Optical Corporation, Southbridge, Mass.

[22] Filed: Apr. 7, 1976

[21] Appl. No.: 674,348

[52] U.S. Cl. .................................................. 3/13
[51] Int. Cl.² ........................ A61F 1/16; A61F 1/24
[58] Field of Search .................... 3/13, 1; 351/160

[56] References Cited  
UNITED STATES PATENTS

| 3,673,616 | 7/1972 | Fedorov et al. | 3/13 |
|---|---|---|---|
| 3,866,249 | 2/1975 | Flom | 3/13 |
| 3,906,551 | 9/1975 | Otter | 3/13 |
| 3,913,148 | 10/1975 | Potthast | 3/13 |

Primary Examiner—Ronald L. Frinks  
Attorney, Agent, or Firm—H. R. Berkenstock, Jr.; William C. Nealon

[57] ABSTRACT

A lens suitable for implantation in an aphakic eye is provided with a supporting system useful in positioning the lens in either the posterior or anterior chamber and which accommodates to normal function of a dynamic pupil. The supporting system includes flexible spring-like members structurally designed to follow a dilating and contracting pupil with negligible force against a normally dilated iris diaphragm while providing for automatic centration in the pupil and permanent longitudinal fixation of the lens under normal and extreme conditions of dilation.

10 Claims, 6 Drawing Figures

ARTIFICIAL INTRAOCULAR LENS AND SUPPORTING SYSTEM THEREFOR

BACKGROUND OF THE INVENTION

1. Field of the Invention:

This invention relates to improvements in ophthalmology and more particularly to supporting systems for artificial intraocular lenses (pseudophakoi) used for correction of aphakia and re-establishment of binocularity in aphakia.

2. Discussion of the Prior Art:

Well-fixed and well-centered intraocular lens implants are known to produce stable retinal images and offer the best chance of re-establishment of binocularity in cases of aphakia.

A characteristic common to presently employed lenses which thwarts the normal activity of the aphakic eye's pupil, however, is the maintenance of a constant minimal pupil size as determined by the radial spacing of posterior projections of non-yielding post-irido loops or clips. A pilocarpine regimen is usually necessary to avoid accidental lens dislocation occurring as a result of pupil dilation.

Supporting systems which can accommodate for normal dilation and contraction of a dynamic pupil have been made the subject of a copending application for patent bearing Ser. No. 587,483 and filing date of June 16, 1975 now U.S. Pat. No. 3,975,779.

These latter systems, having been designed to apply a constant holding force against the pupil margin under maximum normal dilation and beyond (i.e. medically induced abnormal dilation) for purposes of avoiding axial displacement of the pseudophakos, have a disadvantage of tending, in some applications of use, to traumatize the pupil margin and/or produce excessive distortion of the normally circular pupil configuration. These problems, when existent, occur to their greatest extent during pupil contraction, e.g. in response to bright light or artificially induced situations.

Accordingly, an object of the present invention is to overcome the aforesaid and corollary drawbacks of intraocular lens-supporting systems which can accommodate to normal dynamic pupil function and to accomplish this without danger of displacement of the pseudophakos after proper implantation.

It is also an object of the invention to render possible the placement of pseudophakoi in either the anterior chamber of an aphakic eye or the more natural lens position posteriorly of the iris diaphragm; and A more general object is to provide for improvement in structure, function and applicability to the aphakic eye of pseudophakoi which can accommodate to dilation and contraction of the dynamic pupil.

Other objects and advantages of the invention will become more readily apparent from the following summary of the invention and description of the preferred embodiments.

SUMMARY OF THE INVENTION

The invention provides an intraocular lens and lens-supporting system which can be readily arranged to permit implantation either in the anterior or the posterior chamber of an aphakic eye. In the latter situation, implantation immediately behind the iris diaphragm places the artificial lens in approximately the location of the extraction so that danger of corneal damage by the pseudophakos can be minimized, if not eliminated. Provision for fixing the pseudophakos with its lens in the anterior chamber is, however, contemplated for situations where it may be desirable or preferable to do so. The lens-supporting (haptic) section of the pseudophakos comprises a plurality of flexible spring-like members designed to follow the margin of the dynamic pupil while, at the same time, providing longitudinal fixation and centration of the lens.

Each spring-like follower member is anchored adjacent the periphery of the lens and extends therefrom a substantial distance laterally into a looped configuration back to a position forwardly of one of the lens surfaces whereupon it is terminated with a U-shaped clip into which the irido-pupillary margin may be fitted.

Each spring-like follower is preformed so that in a relaxed (not under spring tension) condition its U-shaped clip is located a radial distance from the center of the lens approximately equal to the radial dimension of the pupil margin of an eye which is dilated to or approximately to the maximum size possible without artificial stimulation. Thus, under conditions of normal maximum pupil dilation, the U-shaped clips apply negligible or no force at all against the pupil margin while during pupil contraction the force against the pupil margin at each point of contact of the U-shaped clips is minimal but sufficient to maintain accurate lens centration in the eye. This avoids traumatization of the iris and prevents excessive distortion of the pupil shape during contraction and dilation.

The looped lateral extensions of the pupil follower members and their U-shaped clips prevent accidental disconnection and/or forward or rearward displacement of the pseudophakos when it becomes necessary to medically induce pupil dilation beyond normal limits for intraocular examination.

Details of the invention will become more readily apparent from the following description when taken in conjunction with the accompanying drawings.

IN THE DRAWINGS

DESCRIPTION OF THE PREFERRED EMBODIMENTS

Figure 1:
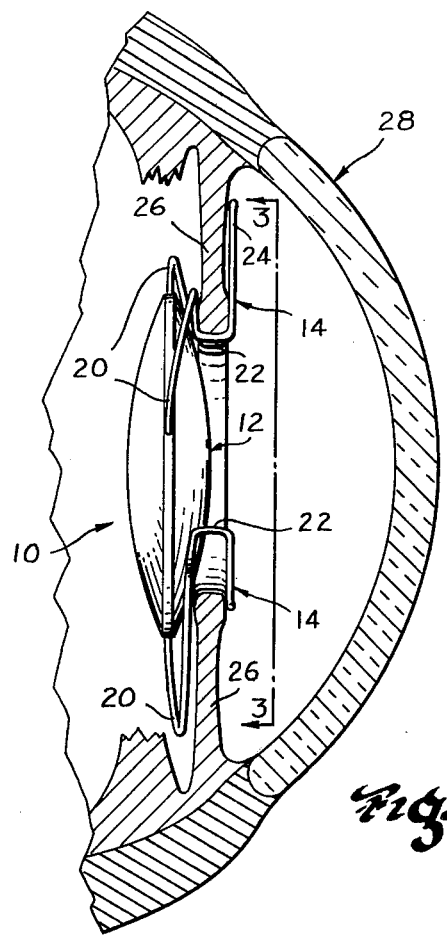
FIG. 1 is an illustration, in side elevation, of a preferred embodiment of a pseudophakos in situ, the eye being shown in cross-section for clarity of illustration.
Figure 2:
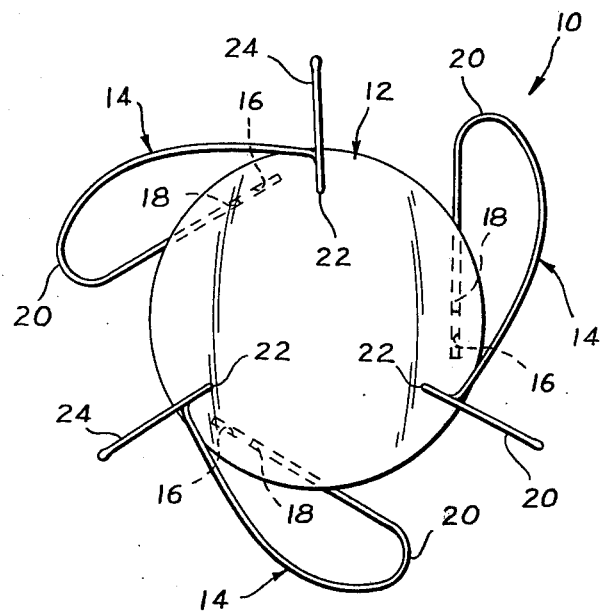
FIG. 2 is a front elevational view of the pseudophakos of FIG. 1.

Referring more particularly to FIGS. 1-4, pseudophakos 10 comprises an optical section (lens 12) and a fastening or haptic section (lens-supporting arms 14).

Lens 12 is formed of a material which is biologically inert, i.e. not susceptible to being absorbed by body fluids and capable of being well tolerated by the human body when implanted. Exemplary materials are quartz, ophthalmic glass, methylmethacrylate resins such as those available under the tradenames "Lucite" and "Plexiglass" and biologically neutral, chemically pure polymethylmethacrylates or biologically inert polymeric materials.

Supporting arms 14 are, for similar reasons of avoiding irritation and/or human body rejection of its components, formed of a bioligically inert material such a platinum, titanium or an extruded polyamide such as nylon.

The supporting arms 14 and their equivalents in modifications of the invention will be described hereinafter as being formed of "wire", it being understood that the term wire as used in this specification and its appendant claims is intended to include strands, strips or rods of biologically inert material whether such material is metallic or plastic and/or whether one or the other is used exclusively throughout the system of arms 14 or the system is made up of both.

Lens 12 is provided with a plurality, preferably at least three, equally radially and circumferentially spaced chordal openings 16 which may be extended completely through or partially into the lens material as illustrated.

Extended into openings 16 and permanently anchored thereinplace are proximal ends 18 of arms 14. Ends 18 of arms 14 may be force fitted or cemented in openings 16 or ends 18 may be terminated with a bead or be otherwise headed so as to provide added anchoring stability. By such means, a displacement of lens material therearound, e.g. by cold flow or with an application or heat and/or ultrasonic vibration will prevent withdrawal and turning of arms 14 in openings 16.

The material selected for arms 14, e.g. from one or more of the aforementioned metals or plastics, is preselected so as to be characteristically spring-like and capable of returning to a preformed configuration or shape when deformed by bending therefrom. Each arm is so preshaped that in its relaxed condition (i.e. not under bending force) it extends from openings 16 a substantial distance laterally away from the edge of lens 12 to a bight 20 wherewith it is looped reversely toward lens 12 in a direction tending toward the anterior surface of the lens and terminating forwardly of the lens. It is further placed under tension toward the forward surface of the lens to prevent undue axial movement of the lens away from its free end in use of the pseudophakos 10.

At the free end of each arm 14 it is formed into the configuration of a U-shaped clip 22 having a relatively long strut-like portion 24 which is smoothly rounded or beaded at its end. Clip 22, in each case, is shaped to accept the marginal portion of the iris 26 of an eye 28 intended to receive pseudophakos 10 substantially in the manner illustrated in FIG. 1.

Figure 3:
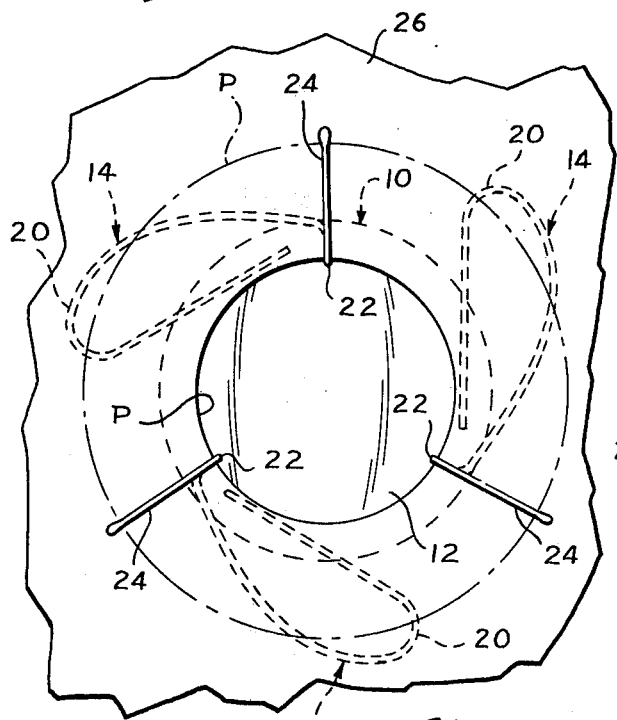
FIG. 3 is a front elevational view of the iris of the eye of FIG. 1 taken generally from the position of line 3—3 and illustrating a condition where the iris, with the pseudophakos in situ, is dilated to maximum normal pupil diameter.
Figure 4:
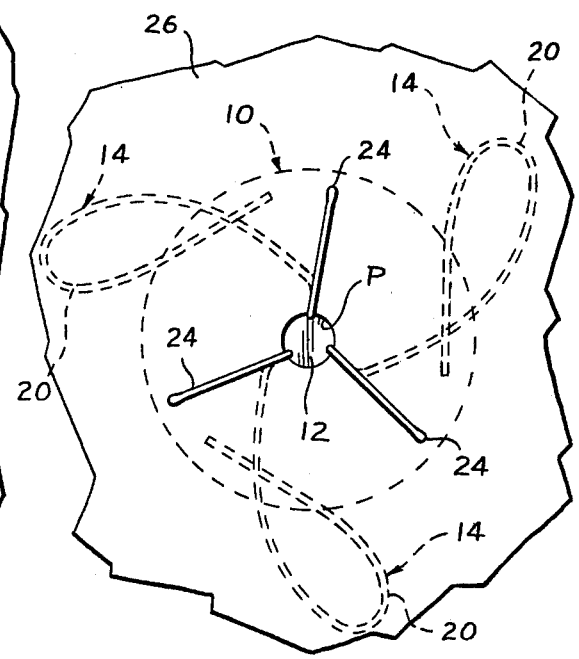
FIG. 4 is a view similar to FIG. 3 but illustrating a condition of substantially minimum pupil dilation (maximum contraction)

In this embodiment of the invention, pseudophakos 10 is positioned posteriorly of iris 26, i.e. approximately at or adjacent to the position originally assumed by the extracted human lens, and clips 22 are fitted over the pupil margin with strut portions 24 thereof extending radially over the anterior surface. of iris 26 (FIGS. 1, 3 and 4).

It should be understood that lens 12 may be placed in the anterior chamber of eye 28 (i.e. forwardly of iris 26) by simply reversing its position in the eye so that strut portions 24 of clips 22 are caused to extend posteriorly of iris diaphragm 26.

A special feature of the present invention which avoids excessive force against and traumatization of the pupil margin of iris diaphragm 26 and/or excessive pupil shape distortion, is best illustrated in FIGS. 3 and 4.

Pupil P is illustrated in FIG. 3 as being dilated to a maximum normal diameter wherein, with clip portions 22 of arms 14 fastened over the pupillary margin of iris diaphragm 26, arms 14 are in their relaxed condition (not under bending tension). In other words, arms 14 are in positions corresponding to those depicted in FIG. 2 before implantation. Lens 12 is thereby automatically centered in pupil P and held against axial displacement by laterally extending portions of arms 14 adjacent bights 20 and by strut portions 24. Bights 20 prevent forward displacement and struts 24 prevent rearward displacement while the aforesaid tension in arms 14 urging them toward the lens surface further avoids tendency for rearward axial displacement of the lens. At the same time and with pupil P at maximum normal dilation as shown, minimal or no force at all is applied to the pupillary margin of iris diaphragm 26. If desired, however, artificial or medically induced dilation to the extent of enlarging pupil P to a size diagrammatically illustrated by dot-dash outline P, or slightly greater, may be effected for purposes of intraocular examination without danger of axial displacement of pseudophakos 10; bights 20 and struts 24 still preventing such displacement.

By affording negligible or no holding force at all against the margin of pupil P at normal maximum dilation as illustrated in FIG. 3, it can be seen that the flexing of arms 14 by contraction of pupil P to the maximum extent normally encountered will effect only slight, non-irritating and substantially non-distorting force against the pupil margin. The long and slender extensions of arms 14 from respective clip portions 22 to points of entry in anchoring openings 16 provide only a gentle pupil following force at the iris margin which maintains a constant centering of lens 12 in pupil P with struts 24 and bights 20 preventing accidental axial displacement of the pseudophakos in eye 28.

It should be understood that the actual force applied by clips 22 against iris diaphragm 26, i.e. the margin of pupil P, during pupil contraction from the maximum condition of normal dilation (FIG. 3) to minimum dilation (FIG. 4) can be preset to desired values by selection of the materials and diametral sizes used for wires making up arms 14. A material and wire size useful according to the invention is titanium of from 0.1 mm to 0.5 mm in diameter and having an extension between a clip 22 and its point of entry into lens 12 or approximately 7 mm.

Figure 5:
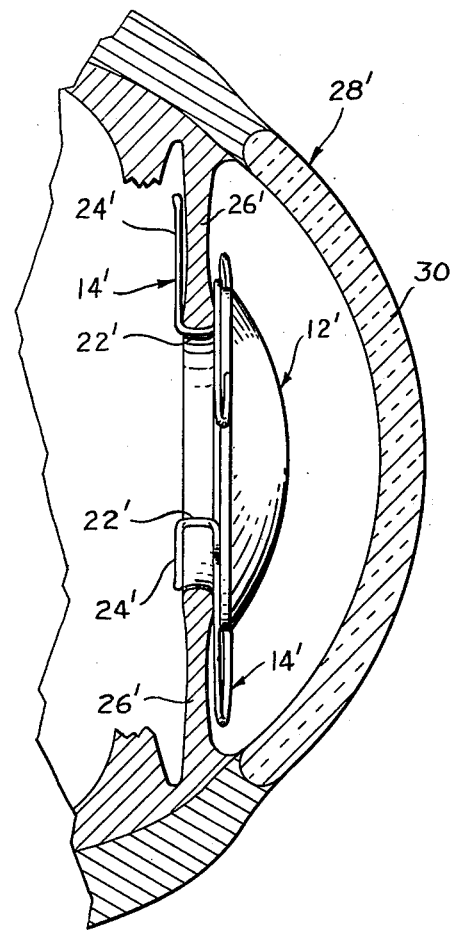
FIG. 5 is a view similar to FIG. 1 but illustrating, in cross-section, a modification of the invention.
Figure 6:
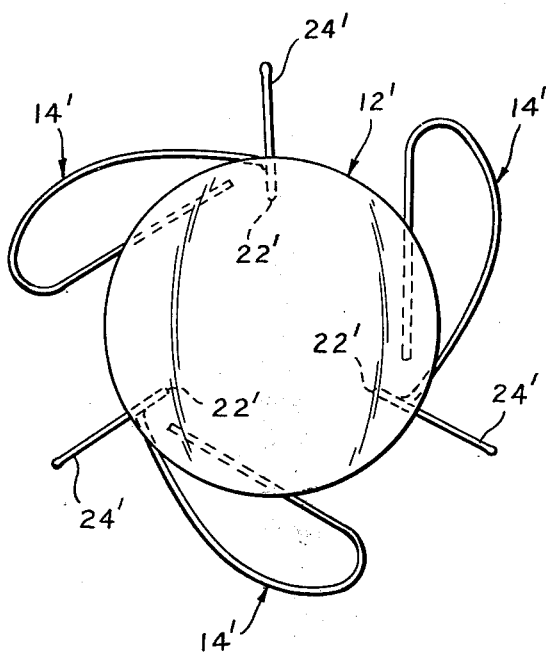
FIG. 6 is a front elevational view of the modified pseudophakos of FIG. 5.

In FIGS. 5 and 6 there is shown a modification of the invention wherein a plano-convex lens 12' is provided with supporting arms 14' of substantially identical configuration and positioning upon lens 12' as are arms 14 of lens 12. In the present case, however, clip portions 22' are disposed immediately rearwardly of lens 12' adjacent its flat posterior surface. While not shown, it should be understood that arms 14' may be directed forwardly of lens 12' with clips 22' located adjacent to its convex surface if it is desired to implant lens 12' behind iris 26' Clips 22' in such a case would be reversed by bending so that strut portions 24' thereof would be foremost, e.g. as in pseudophakos 10 of FIGS. 1-4.

We claim:
1. A pseudophakos comprising:

a lens having oppositely disposed anterior and posterior optically finished side surfaces;

a plurality of slender and resilient supporting arms affixed to said lens adjacent its periphery, said arms each being of a looped configuration including a bight disposed a substantial distance laterally away from said periphery of said lens and a free end positioned adjacent one of said side surface of said lens when said arm is in a relaxed condition;

said free end of said arm being in the configuration of a clip for receiving the irido-pupillary margin of an eye when the pseudophakos is implanted for use and wherewith said lens may be centered relative to the pupil, each free end of each arm when in said relaxed condition being approximately equally radially spaced from said center of said lens an amount approximately corresponding to the radial dimension of said pupil when said pupil is at approximately maximum normal dilation whereby under such condition of pupil dilation said clips do not apply appreciable force against said pupil margin while at maximum pupil contraction only minimal gentle holding force is applied.

2. A pseudophakos according to claim 1 wherein each of said clips is terminated with a laterally directed strut portion of substantial length, said strut portion and said bight of a corresponding one of said arms being intended for disposition one forwardly of and one rearwardly of the iris of an eye receiving said pseudophakos for preventing accidental axial displacement of said pseudophakos during use thereof.

3. A pseudophakos according to claim 2 wherein the lateral extensions of said strut portions and of said bights from a point centrally of said lens are greater than the maximum radial dimmension of pupil dilation normally used in artificial stimulation situations for intraocular examination purposes.

4. A pseudophakos according to claim 1 wherein said anterior and posterior lens surfaces are convexly curved and said pseudophakos is reversible for fixation in either the posterior or anterior chambers of the eye.

5. A pseudophakos according to claim 1 wherein one of said sides of said lens is plano and the other side is convexly curved.

6. A pseudophakos according to claim 5 wherein said free end of each of said clips is positioned adjacent said convexly curved side of said lens.

7. A pseudophakos according to claim 5 wherein said free end of each of said clips is positioned adjacent said plano side of said lens.

8. A pseudophakos according to claim 1 wherein said lens is formed of glass.

9. A pseudophakos according to claim 1 wherein said lens is formed of plastic material.

10. A pseudophakos according to claim 1 wherein said arms are affixed in openings extending into said lens adjacent its periphery.

* * * * *